(12) United States Patent
Pech (10) Patent No.: US 9,517,078 B2
(45) Date of Patent: Dec. 13, 2016

(54) BONE MILLING TOOL, ASSORTED SET AND SYSTEM WITH BONE MILLING TOOL

(71) Applicant: ZIMMER GMBH, Winterthur (CH)

(72) Inventor: Uwe Pech, Tuttlingen (DE)

(73) Assignee: ZIMMER GMBH (CH)

( * ) Notice: Subject to any disclaimer, the term of this patent is extended or adjusted under 35 U.S.C. 154(b) by 184 days.

(21) Appl. No.: 13/747,982

(22) Filed: Jan. 23, 2013

(65) Prior Publication Data

US 2013/0197524 A1 Aug. 1, 2013

(30) Foreign Application Priority Data

Jan. 24, 2012 (DE) ........................ 10 2012 100 565

(51) Int. Cl.
*A61B 17/16* (2006.01)
*A61B 17/88* (2006.01)

(52) U.S. Cl.
CPC ....... *A61B 17/1682* (2013.01); *A61B 17/1617* (2013.01); *A61B 17/88* (2013.01)

(58) Field of Classification Search
CPC .................... A61B 17/1617; A61B 17/1682
USPC ...................................................... 606/79–85
See application file for complete search history.

(56) References Cited

U.S. PATENT DOCUMENTS

| | | | | |
|---|---|---|---|---|
| 2,426,526 A | * | 8/1947 | Rutishauser | F02K 9/343 439/39 |
| 3,397,012 A | * | 8/1968 | Krekeler | E21C 35/1933 172/713 |
| 3,535,204 A | * | 10/1970 | Truxa | D21F 1/483 162/352 |
| 3,630,204 A | | 12/1971 | Fishbein | |
| RE28,895 E | * | 7/1976 | Noiles | A61F 2/30728 623/22.31 |
| 4,023,572 A | | 5/1977 | Weigand et al. | |
| 4,116,200 A | * | 9/1978 | Braun | A61B 17/1666 30/276 |
| 4,380,090 A | * | 4/1983 | Ramos | A61F 2/32 623/22.2 |
| 4,621,637 A | * | 11/1986 | Fishbein | A61B 17/1666 408/227 |
| 4,795,468 A | * | 1/1989 | Hodorek | A61F 2/389 623/20.28 |
| 5,171,313 A | * | 12/1992 | Salyer | A61B 17/1617 606/100 |

(Continued)

FOREIGN PATENT DOCUMENTS

DE 60107285 T2 12/2005
WO 0249516 A1 6/2002

OTHER PUBLICATIONS

European Search Report for EP Application No. 12193362.6 dated May 7, 2013.

*Primary Examiner* — Zade Coley
(74) *Attorney, Agent, or Firm* — Schwegman Lundberg & Woessner, P.A.

(57) ABSTRACT

A surgical bone milling tool, in particular for the arthrodesis of a, preferably the first, metatarsophalangeal joint, with a rotatable milling cutter holder and at least one milling cutter for the production of a concave or convex milling contour in the bone, which is able to be fixed detachably on the milling cutter holder by a fixing element. Provision is made that the fixing element comprises a detent having a spring element provided for the detachable engagement of the milling cutter on the milling cutter holder.

19 Claims, 12 Drawing Sheets

(56) References Cited

U.S. PATENT DOCUMENTS

| | | | | |
|---|---|---|---|---|
| 5,236,433 A | * | 8/1993 | Salyer | A61B 17/1666 606/80 |
| 5,620,339 A | * | 4/1997 | Gray | H01R 4/489 439/578 |
| 5,755,719 A | * | 5/1998 | Frieze | A61B 17/1666 606/81 |
| 5,976,144 A | * | 11/1999 | Fishbein | A61B 17/1684 606/70 |
| 5,993,453 A | * | 11/1999 | Bullara | A61B 17/16 606/79 |
| 6,114,757 A | * | 9/2000 | DelPrete | H01L 23/32 257/678 |
| 6,436,101 B1 | * | 8/2002 | Hamada | A61B 17/1604 606/85 |
| 6,979,335 B2 | | 12/2005 | Lechot | |
| 6,991,407 B2 | * | 1/2006 | Dannehl | E21D 23/0436 405/290 |
| 7,011,662 B2 | | 3/2006 | Lechot et al. | |
| 7,837,686 B1 | * | 11/2010 | Tulkis | A61B 17/1666 606/81 |
| 7,992,945 B2 | * | 8/2011 | Hall | E21C 35/183 299/105 |
| 2004/0049199 A1 | * | 3/2004 | Lechot | A61B 17/1666 606/80 |
| 2012/0191099 A1 | * | 7/2012 | Victor | A61B 17/1666 606/81 |

\* cited by examiner

BONE MILLING TOOL, ASSORTED SET AND SYSTEM WITH BONE MILLING TOOL

BACKGROUND OF THE INVENTION

The invention relates to a surgical bone milling tool, in particular a so-called cup-and-cone milling tool, according to the introductory clause of Claim 1, in particular for the arthrodesis of a, preferably the first, metatarsophalangeal joint, with a rotatable milling cutter holder and at least one milling cutter for the production of a concave or convex milling contour in the bone, which is able to be detachably fixed to the milling cutter holder by fixing means. The invention further relates to an assorted set with such a bone milling tool according to Claim 14 and a system with a bone milling tool and a releasing tool according to Claim 15.

Generic surgical bone milling tools, so-called cup-and-cone milling tools, have been known for a long time. These are used in foot surgery primarily in the arthrodesis of the first metatarsophalangeal joint. Here, firstly a first bone part is milled in a concave manner and a second bone part is milled in a correspondingly convex manner, whereupon then the bone parts are joined together in the manner of a ball-socket connection and are then fixed, so that the first and second bone parts grow together.

The (foot) bone milling tools available on the market are generally one-piece, i.e. are constructed from one casting or respectively on one piece.

In addition to these one-piece surgical bone milling tools, bone milling tools have become known in which the milling cutter is exchangeable, for example in order to be able to sharpen it in a facilitated manner. U.S. Pat. No. 4,621,637 describes such a surgical bone milling tool. The known bone milling tool has a milling cutter holder, which is able to be driven by a corresponding electric tool.

Two milling cutters are able to be inserted in openings of the milling cutter holder on the front face, wherein the fixing, i.e. axial securing of the milling cutters on the milling cutter holder takes place via a coupling piece, which is able to be fixed in corresponding openings in the milling cutter holder via elastomer rings. A disadvantage in the known surgical bone milling tool is its complex structure and the large number of individual parts which are required, which makes assembly and dismantling and hence also the cleanability difficult.

An alternative surgical bone milling tool with a removable milling cutter is known from U.S. Pat. No. 3,630,204. For axially securing the milling cutter, a fixing screw is provided which is able to be screwed laterally in an internal threaded hole of the milling cutter holder and penetrates a fixing opening of the milling cutter. Here, also, the assembly and dismantling is difficult or respectively time-consuming, because it is necessary, for securing or respectively releasing, to screw or respectively unscrew a fixing screw. Furthermore, the cleanability is in need of improvement.

Proceeding from the above-mentioned prior art, the invention is based on the problem of indicating an improved surgical bone milling tool with an exchangeable milling cutter, wherein the bone milling tool is to be distinguished by a structurally simple construction, and especially by a simple capability of being assembled and dismantled. Furthermore, the bone milling tool is to have as few individual parts as possible and be able to be cleaned readily. In addition, the problem consists in indicating an assorted set enabling a high degree of flexibility, with a bone milling tool which is improved in such a manner, and a system of a bone milling tool and of a releasing tool, which displays a capability of the bone milling tool to be simply and quickly dismantled, or respectively a simple exchanging of the milling cutter.

SUMMARY OF THE INVENTION

This problem is solved with regard to the bone milling tool, preferably constructed from titanium and/or surgical steel.

The invention is based on the idea of securing the milling cutter directly on the milling cutter holder with the aid of detent means, wherein it is particularly preferred if additional fixing means, in particular screws or removable mountings, such as for example a holding dome described in U.S. Pat. No. 4,621,637, are dispensed with. The direct engaging of the milling cutter via a spring element involves considerable advantages. Thus, the number of parts is reduced to a minimum; in addition to at least one milling cutter and a milling cutter holder, preferably only one spring element, if applicable also several spring elements are required. Not only is a structurally simple construction guaranteed here—also a good cleanability is a direct result. Preferably, the milling cutter according to the invention is constructed as a hand bone milling tool or as a foot bone milling tool for the arthrodesis of a, in particular the first, metatarsophalangeal joint. According to the configuration of the milling cutter, joint surfaces can also be processed or respectively renewed with the bone milling tool.

An embodiment of the bone milling tool is particularly expedient, in which the at least one, preferably exclusively one, spring element is constructed and arranged such that the latter, on the securing process of the milling cutter, is able to be tensioned in radial direction, i.e. is movable contrary to the elastic force of the spring element and in the engaged state is held with at least reduced tension or without tension in a detent recess. According to the arrangement of the spring element, the detent recess, constructed preferably as at least one detent groove, can be arranged on the milling cutter or on the milling cutter holder. Preferably, the spring element is also temporarily tensioned on releasing from the detent position, wherein particularly preferably both on securing and also on releasing, the spring tension of the spring element must be overcome. It is particularly expedient when the spring element acts with elastic force in radial direction inwards or outwards on the milling cutter and/or the milling cutter holder during the assembly- and/or dismantling process.

There are various possibilities with regard to the arrangement or respectively positioning of the spring element. According to a first, preferred variant, the spring element is secured in particular in a groove, more preferably a peripheral groove of the milling cutter holder, and on securing of the milling cutter is tensioned by direct interaction with the milling cutter, wherein the spring element is preferably at least less tensioned in the detention position than at a time during the securing process. It is most particularly preferred here if the milling cutter acts upon the spring element with elastic force in radial direction outwards on securing and/or releasing, wherein also an embodiment is able to be realized in which the action of force takes place in radial direction inwards.

In a further variant, the spring element is secured on the milling cutter and is tensioned by direct interaction with the milling cutter holder, preferably then in radial direction inwards, wherein also alternatively a tension in radial direction outwards is possible. In addition, it is conceivable to realize both above-mentioned variants (with two different spring elements) together.

An embodiment is particularly preferred, in which the milling cutter and/or the milling cutter holder penetrate(s) the spring element in the engaged state axially inwards, or embrace it externally.

According to a particularly preferred variant embodiment, as, in particular sole, spring element at least one, preferably metallic, spring ring is provided, which further preferably develops its spring effect owing to a slotted configuration. Instead of the provision of a spring ring as spring element which is able to be elastically expanded and/or compressed, it is conceivable to provide at least two springs, for example of part-ring shape, preferably spaced apart in peripheral direction, which further preferably are able to be tensioned in radial direction inwards and/or outwards during the securing and/or releasing of the milling cutter.

In order to further simplify the assembly of the milling cutter on the milling cutter holder, in a further development of the invention provision is advantageously made that for the radial tensioning of the milling cutter during the securing—according to the arrangement of the spring element on the milling cutter holder or on the milling cutter, a leading chamfer is provided on the milling cutter or respectively on the milling cutter holder, by which the spring element is able to be acted upon, in particular in radial direction outwards or inwards with a relative movement by a force, in particular a radial force and is thereby able to be tensioned in order to then be received in the detent recess after overcoming the leading chamfer. In order to reliably prevent an unintentional releasing of the milling cutter, it is particularly expedient if no such leading chamfer, or a less steep, i.e. difficult to overcome, leading chamfer is provided for releasing the milling cutter.

It has proved to be particularly expedient if in particular a lateral tool mount (opening) is provided on the milling cutter holder to receive a releasing tool, wherein the milling cutter extends in particular axially into this mount, so that the milling cutter in the mount is able to be acted upon by force in axial direction in a releasing direction away from the milling cutter holder by means of the releasing tool. This can be realized for example in that a leading chamfer is provided on the releasing tool, which leading chamfer, by inserting of the releasing tool into the mount, comes into interaction with the milling cutter and pushes the latter upwards. Alternatively, it is conceivable to coordinate the releasing tool and mount with one another such that the releasing tool is able to be introduced in particular free of tension into the mount and is rotatable there, and thereby acts upon the milling cutter with releasing force in axial direction.

It is particularly expedient if the spring element exclusively has the task or respectively is constructed so that it secures the milling cutter against axial releasing. Preferably, in addition form-fitting means are provided, which cooperate with the milling cutter or respectively are coordinated therewith such that a twisting of the milling cutter relative to the milling cutter holder in peripheral direction is reliably prevented. In the simplest case, the form-fitting means are formed by an axial guide for the milling cutter, into which the milling cutter, preferably cruciform in an axial projection, as will be further explained later, can be inserted. In the case of a concave milling cutter, it is preferred if the latter is secured in a radially outer region in peripheral direction, for example through radial slots in a peripheral wall of the milling cutter holder. In the case of the convex milling cutter, it is preferred if the guide or respectively anti-twist protection is arranged in a radially lower region.

It has proved to be particularly expedient if the spring element, in particular constructed as a spring ring, penetrates the above-mentioned anti-twist protection, which is preferably constructed as an axial guide, in peripheral direction so that the spring element engages with the milling cutter or with the spring holder in the region of the anti-rotation protection.

Various possibilities exist with regard to the configuration of the milling cutter. To achieve an optimum milling result, it has proved to be particularly advantageous if a milling cutter is used which is cruciform in the axial projection. The milling cutter can be constructed in a single piece or can consist of several, in particular two parts, further preferably able to be inserted into one another axially. It is also possible to connect two cutter parts, in particular cutter discs, permanently securely with one another by gluing or welding. With regard to the milling result and the resulting surface structure, it has proved furthermore to be advantageous to construct the milling cutter edge, at least partially, preferably completely, in the form of a serration, because accordingly uneven bone structures promote a growing together, wherein according to a first variant as a whole a symmetrical serration is selected, in which wave crests of two cutter sections which are spaced apart from one another in peripheral direction lie on the respectively same radius, likewise the wave troughs respectively adjacent thereto. According to a second variant, an asymmetrical cut is selected, in order to minimize the unevennesses in the bone. In the case of an asymmetrical serration, adjacent wave peaks in peripheral direction do not lie on the same radius, but rather are arranged radially offset, wherein it is particularly preferred if at least one wave peak of a first cutter section lies on the same radius as a wave trough which is spaced apart in peripheral direction.

Conventional bone milling tools frequently have an opening to receive a Kirschner wire, wherein hereby the exposure direction is precisely predefined. In further development of the invention, instead of such a Kirschner wire opening, an in particular small centring point is provided, whereby the operator is substantially more flexible during milling of the bone surfaces—this can be used with horizontally rotating movements, so that exact bone surfaces can be milled in one working step.

The invention also specifies an assorted set, comprising at least one bone milling tool according to the invention, wherein the assorted set comprises in addition to at least one milling cutter holder, at least two milling cutters able to be used with the milling cutter holder, which are differently constructed, in particular in order to be able to carry out convex or concave millings of differing size. In particular, the assorted set comprises at least two concave cutters differing in their milling diameter or at least two differing convex cutters. It is therefore possible to use, with one and the same milling cutter holder, at least two differing, preferably more than two differing milling cutters. The differing milling cutters of an assorted set are constructed identically with regard to the interface with the milling cutter holder and preferably differ only in the edge geometry.

Most particularly preferably, the assorted set comprises at least two differing concave cutters or convex cutters from the following cutter group with a maximum blade diameter of 12 mm, 14 mm, 16 mm, 19 mm, 21 mm and/or 23 mm.

The invention further specifies a system, comprising a bone milling tool constructed according to the concept of the invention, and a releasing tool, which is able to be introduced into an in particular lateral mount of the milling cutter, wherein the milling cutter in the engaged state with the milling cutter holder extends into the mount, in particular perpendicularly to a longitudinal extent of the mount, such that the milling cutter is able to be acted upon by force axially in a releasing direction by means of the releasing tool, in particular by inserting and/or twisting the releasing tool into or respectively in the mount, such that the milling instrument tensions the spring element in radial direction, in order to come free from the engagement. In the realization of a release by twisting, it is preferred if the mount has a circular peripheral contour and the releasing tool has a corresponding pitch circle contour with a flattened section, which enables a pushing under the milling cutter, whereby by twisting the releasing tool the pitch circle section comes in contact with the milling cutter and acts upon this with force axially.

BRIEF DESCRIPTION OF THE DRAWINGS

Further advantages, features and details of the invention will emerge from the following description of preferred example embodiments and with the aid of the drawings.

These show in.

DETAILED DESCRIPTION

In the figures, identical elements and elements with identical function are marked by identical reference numbers.

A first example embodiment of a surgical bone milling tool 1 is shown in FIG. 1a to 1f. This comprises a milling cutter holder 2, rotatable by means of an electric tool, which milling cutter holder has in the region of its rear, or respectively in the drawing lower end, a drive 3 for cooperating with such a tool. The milling means holder 2 carries on the side facing away from the drive 3 a milling cutter 4, in the practical example embodiment a concave milling cutter 4 for the production of convex millings.

Figure 1A:
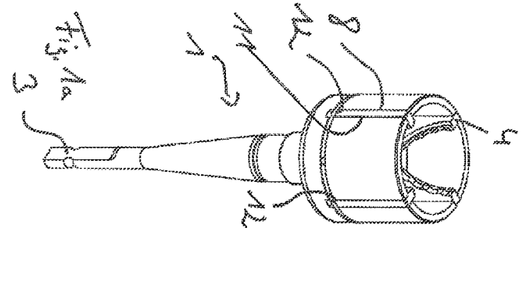
FIG. 1a: a perspective oblique view of an assembled surgical (foot) bone milling tool with a concave milling cutter or respectively with a milling cutter for the production of a convex milling.

The milling cutter 4 has four blade sections 5a to 5d offset by respectively 90° to one another, in the centre of which a centring point 6 is situated.

The milling cutter 4 is secured exclusively by engaging in axial direction with the aid of fixing means 7 which are to be explained further below, or respectively is detachably secured on the milling cutter holder. As anti-twist protection, form-fitting means 8 are provided in the form of axial guides, which reliably prevent a twisting of the milling cutter 4 relative to the milling cutter holder 2. The fixing means 7 comprise a, here single, spring element 9 constructed as a spring ring, which is held in an (outer) peripheral groove 10 of the milling cutter holder 2. The spring element 9 penetrates in peripheral direction axial guides 11 for the milling cutter 4 and lies in the region of these axial guides 11 in the engaged state in detent recesses 12 on the peripheral side in the milling cutter 4 and secures the latter in axial direction. As can be seen from FIG. 1a to 1f, the spring element 9, constructed as a spring ring, is provided at a peripheral location with a slot 13, i.e. is interrupted and thus be expanded in an elastic manner.

Figure 1B:
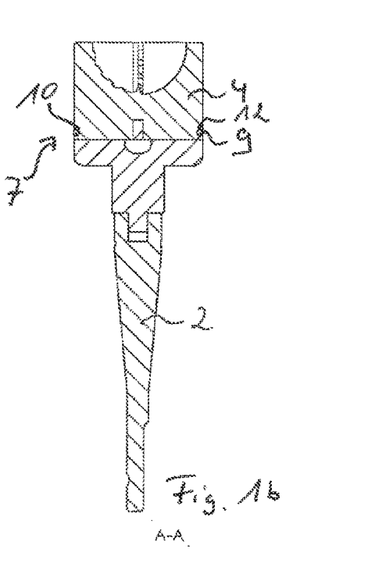
FIG. 1b to FIG. 1f: different two-dimensional views, partially in section, of the bone milling tool according to FIG. 1a, FIG. 2a to FIG. 2g: different views of the concave milling cutter for a bone milling tool according to FIG. 1a to 1f, wherein for clarification the spring element secured on the milling cutter which is not illustrated in FIG. 2a to 2g is illustrated in engaged state, FIG. 3a a perspective view of an alternative (foot) surgical bone milling tool with a convex milling cutter for the production of concave millings.
Figure 1C:
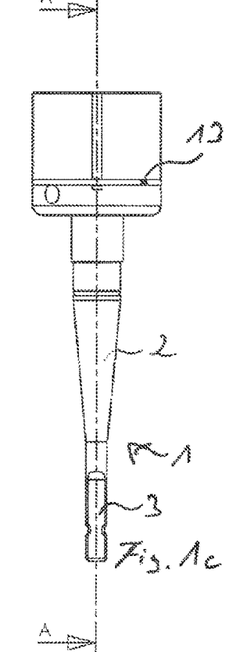
Figure 1D:
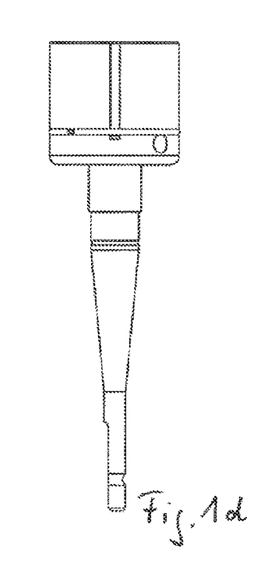
Figure 1E:
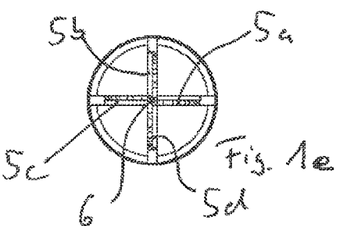
Figure 1F:
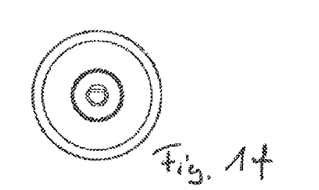

As can be seen in particular from the sectional illustration according to FIG. 1b, the milling cutter 4 penetrates the spring element 9 in the engaged state in axial direction and embraces the spring element 9 partially from the interior radially by receiving the spring element 9 in the four detent recesses which are offset to one another by 90°.

In FIG. 2a to 2g, the milling cutter 4 of the bone milling tool 1 according to FIG. 1a to 1f is shown in detail in different views, together with the spring element 9 actually secured on the milling cutter holder 2, which spring element is illustrated in the engaged position, i.e. received in the four detent recesses 12 of the milling cutter 4.

Figure 2A:
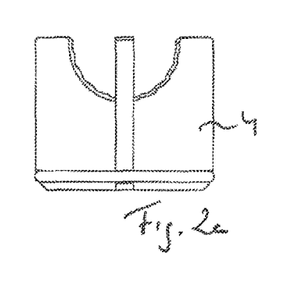
Figure 2B:
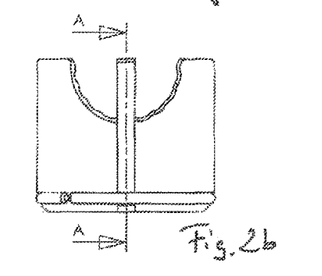
Figure 2C:
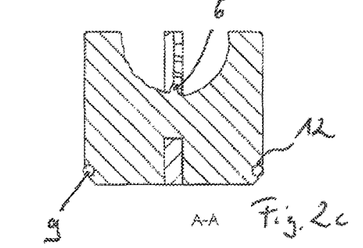
Figure 2D:
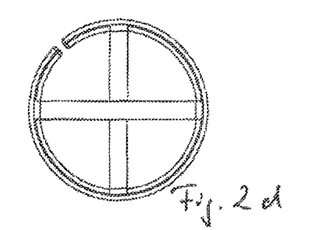
Figure 2E:
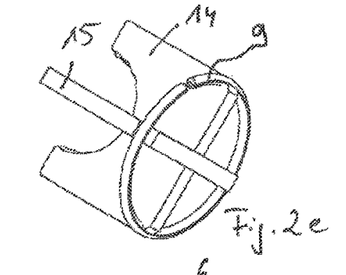
Figure 2G:
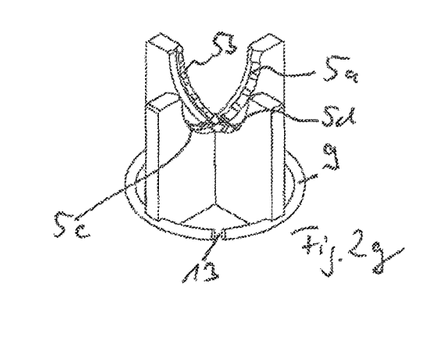
Figure 3A:
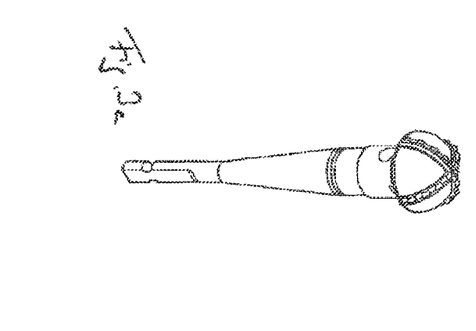
Figure 3B:
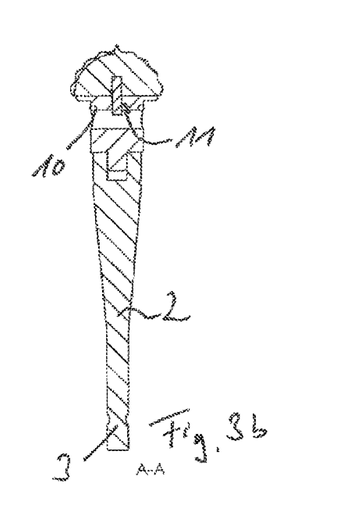
FIG. 3b to FIG. 3f: different two-dimensional views, partially in section, of the bone milling tool according to FIG. 3a, FIG. 4a to FIG. 4h: different views, partially in section, of a convex milling cutter for a bone milling tool according to FIG. 3a to 3e, wherein here also in an analogous manner to FIG. 2a to 2e the spring element secured on the milling cutter holder is illustrated in engaged state.
Figure 3C:
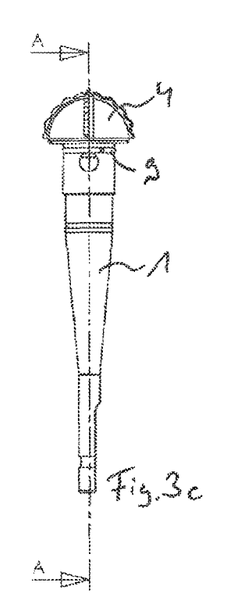
Figure 3D:
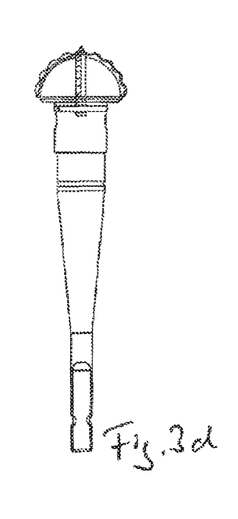
Figure 3E:
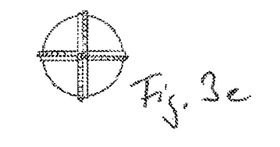
Figure 3F:
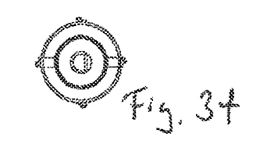
Figure 4A:
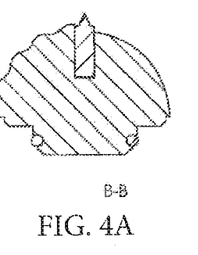
Figure 4B:
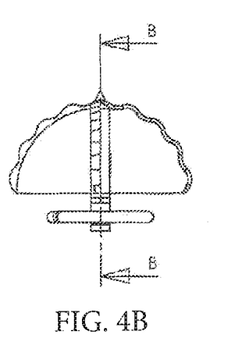
Figure 4C:
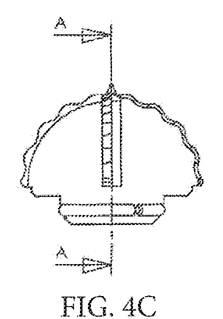
Figure 4D:
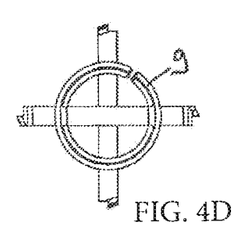
Figure 4E:
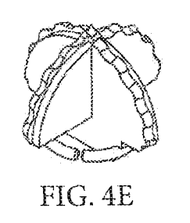
Figure 4F:
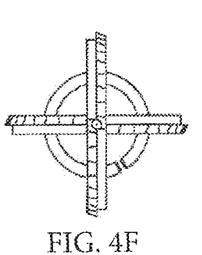
Figure 4G:
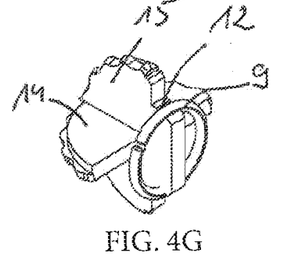
Figure 4H:
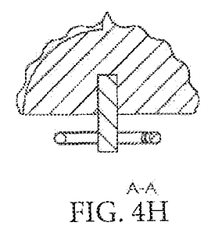

It can be seen that the milling cutter 4 is composed of a first and a second cutter part 14, 15, wherein the cutter parts 14, 15 intersect each other. Alternatively, the cutter parts 14, 15 can be placed detachably in one another or can be permanently connected securely with one another, for example by gluing or welding. A one-piece embodiment of the milling cutter 4 is also theoretically conceivable.

The cutter parts 14, 15 have in an inner region the four blade sections 5a to 5d and are contoured in a straight line on their outer periphery, in the manner of plate sides. With these plate sides the cutter parts 14, can be received in these associated axial guides 11 by axial insertion, wherein the axial guides surround the cutter parts 14, 15 in peripheral direction, in order to thus reliably prevent a twisting of the milling cutter 4 relative to the milling cutter holder 2. In the region of these axial guides, the milling cutter 4 is engaged i.e. at a total of four locations with the spring element 9 which is constructed as am annular spring element.

An alternative bone milling tool 1 is illustrated in FIG. 3a to 3f, which is constructed according to a similar principle to the bone milling tool according to FIG. 1a to 1f, so that to avoid repetitions, reference is to be made to the above figures with associated description with regard to commonalities. Essentially, differences are to be entered into below.

It can be seen that the milling cutter 4 is constructed as a convex cutter for the production of concave millings. Also in the embodiment according to FIG. 3a to 3f, the spring element 9, constructed as an annular spring element, is received in a corresponding peripheral groove 10 of the milling means holder 2 and is penetrated in the engaged state in axial direction by the milling cutter 4, which is guided in a radially inner region axially in a central axial guide 11.

Figure 5:
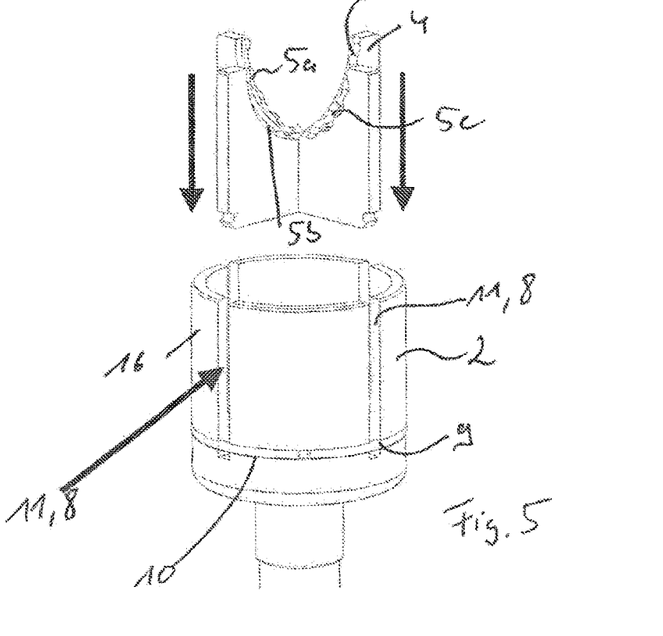
FIG. 5 to FIG. 8: individual steps and details of the engaging securing of a milling cutter on a milling cutter holder.

In FIG. 4a to 4h different illustrations of the convex milling cutter 2 are shown, which is engaged with the spring element 9, which is received for this in two diametrically opposed detent recesses 12 on the peripheral side. The spring element 9 is penetrated axially in the engaged state by two cutter parts 14, 15, which can be placed detachably adjacent to one another in an analogous manner to the other example embodiment, or can be permanently connected securely with one another. In the example embodiment which is shown, only the second cutter part 15 penetrates the spring element and is received in the milling holder 2 in the above-mentioned axial guide. With the aid of FIG. 5 to 8 the assembly process is explained by way of example by means of a bone milling tool with a concave milling cutter. Firstly in FIG. 5 the milling cutter holder 2 is to be seen with its form-fitting means 8, constructed as axial guides 11, for anti-twist protection of the milling cutter 4, which is moved from above in axial direction, indicated by two parallel arrows, towards the milling cutter holder 2, and namely such that the milling cutter, which is cruciform in the axial projection, is received on the edge side in the axial guides 11. In FIG. 5 it can be seen very clearly that in the example embodiment which is shown, the axial guides 11 are delimited by linear interruptions of a hollow-cylindrical peripheral wall 16, which surround the blade sections 5a to 5d radially externally in the assembled state.

It can be seen furthermore from FIG. 5 that the spring element 9, constructed as a metallic spring ring, is received in the peripheral groove 10 of the peripheral wall 11 and penetrates the axial guides 11 in peripheral direction.

Figure 6A:
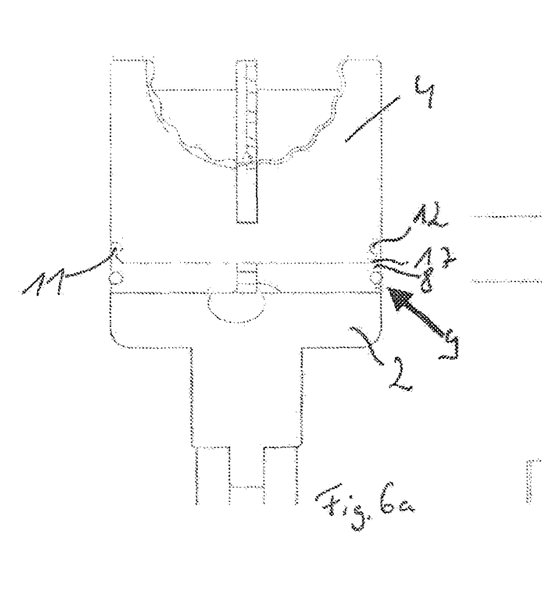
Figure 6B:
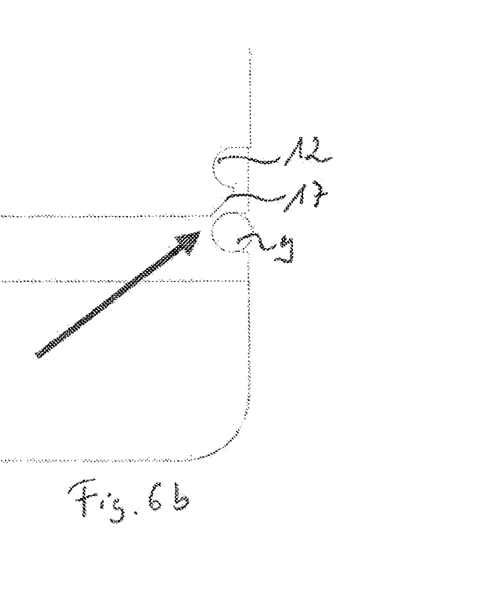

As can be seen from the next step according to the illustrations in accordance with FIGS. 6a and 6b, the milling cutter 4 is provided with a total of 4 leading chamfers 17, which are arranged such that by axial force application of the milling cutter 4 a radial force component results onto the spring element 9, which presses the latter in radial direction outwards during the assembly process and thereby tensions it temporarily, until the leading chamfer 17 is overcome and the spring element 9 can snap in radial direction inwards back into the detent recesses 12 in the region of the axial guides 9.

Figure 7:
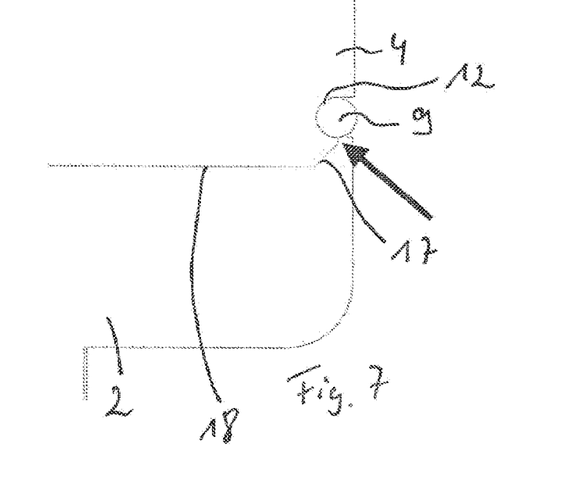

In FIG. 7 the leading chamfer 17 is overcome, the milling cutter 4 lies axially on a contact surface 18 of the milling cutter holder 2 and the spring element 9 lies, preferably tightly in a tensioned manner, in any case less tensioned than during the assembly process or respectively during the abutting of the spring element 9, against the leading chamfers 17 in the detent recesses 12.

Figure 8:
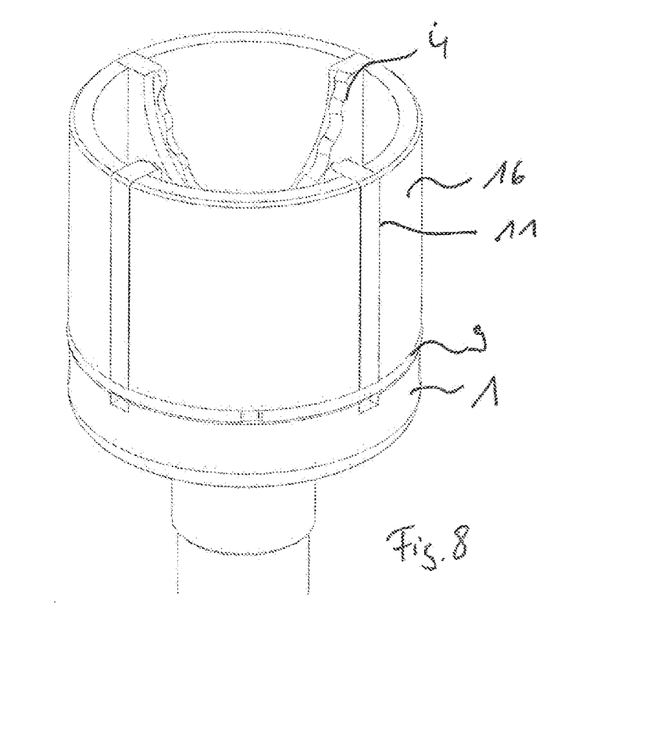

In other words, the milling cutter 4 engages with a lower wall of the detent recess 12 under the spring element 9, whereby the milling cutter 4 is secured against axial lifting from the milling cutter holder 2. FIG. 8 shows in part the assembled bone milling tool 1 with the milling cutter 4, which is secured against rotation in peripheral direction in the axial guides 11 of the peripheral wall 16 and is secured by the spring element 9 in axial direction.

By means of FIG. 9 to 16, a preferred releasing process with the aid of a system, comprising a bone milling tool 1 and a releasing tool 19, is now described.

Figure 9:
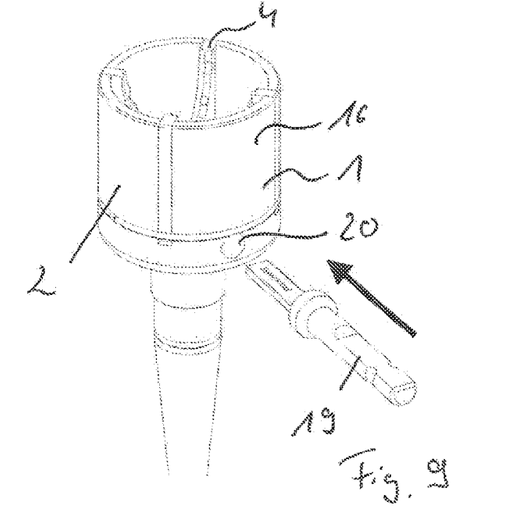
FIG. 9 to FIG. 16: individual steps and details of the dismantling of the milling cutter from the milling cutter holder.
Figure 10:
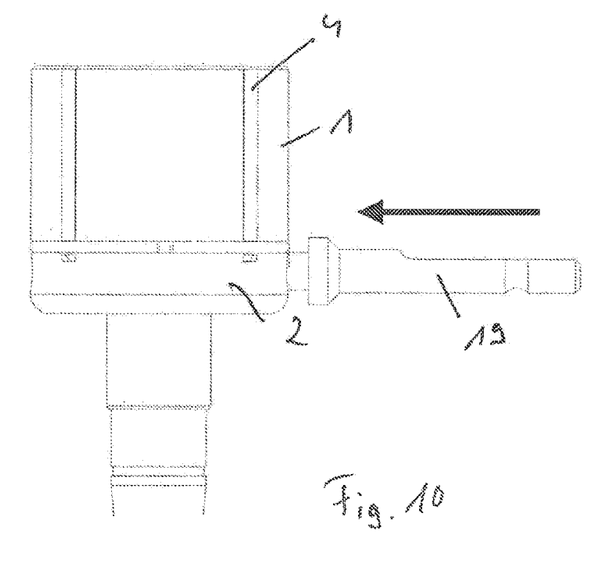

A lateral mount 20, contoured in the form of an annular ring in cross section, can be seen in the peripheral wall 16 of the milling cutter holder 2, into which the releasing tool 19 is able to be introduced in the illustrated arrow direction.

The releasing tool 19 can therefore be guided beneath the milling cutter 4. The releasing tool 19 is introduced up to the stop, wherein the introducing process can be seen in more detail in FIG. 10.

Figure 11:
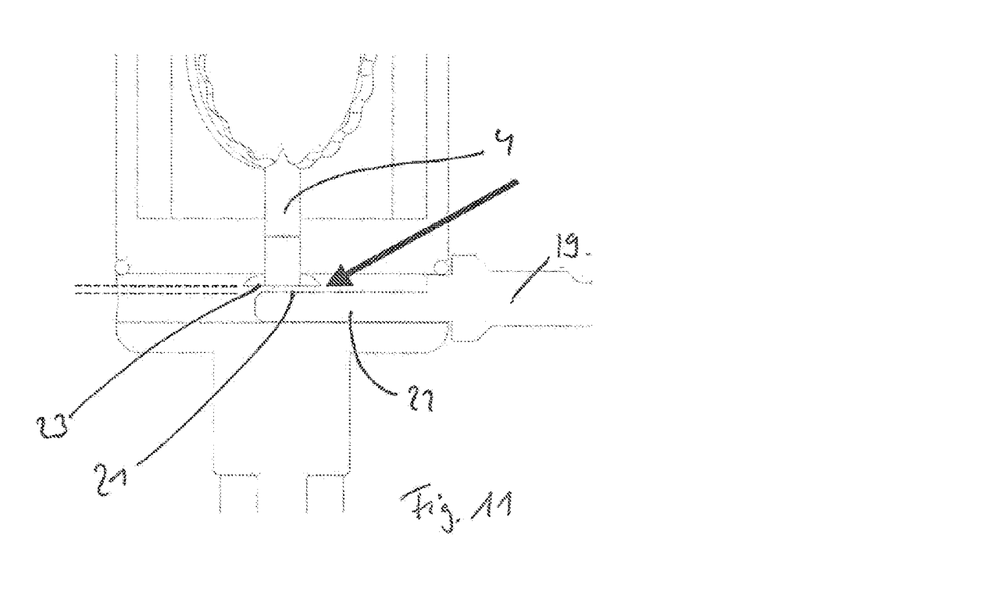
Figure 12:
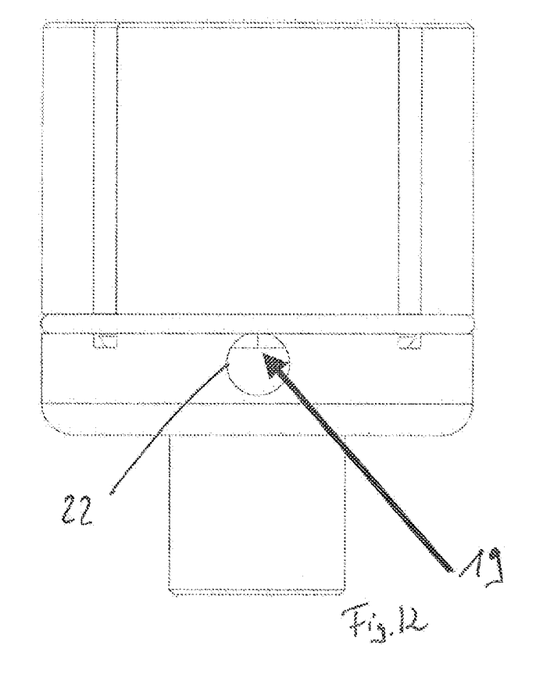

From the sectional view according to FIG. 11 and the side view according to FIG. 12, it can be seen that the introduction section 22 of the releasing tool 12 is constructed so as to be flattened, so that an upper side 21 is initially spaced apart axially from an underside of the milling cutter 4 which is projecting axially into the mount 20 (mount channel). From the side view, it can be readily seen that the introduction section 22 has in cross-section the shape of a truncated cylinder, wherein the lower solid material section provides for a congruent mounting and guidance on the inner periphery of the mount 22.

Figure 13:
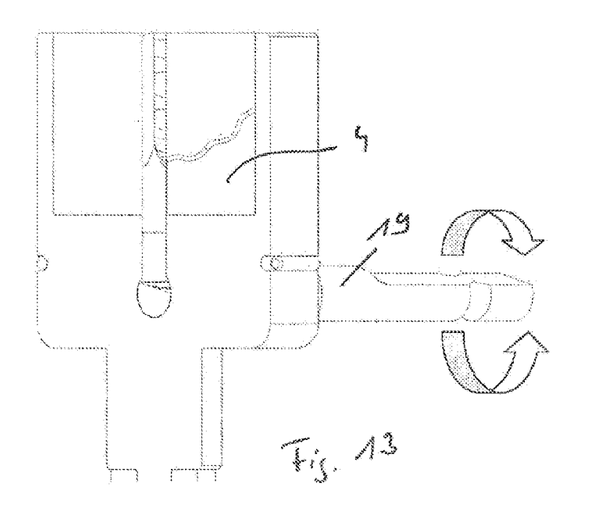
Figure 14:
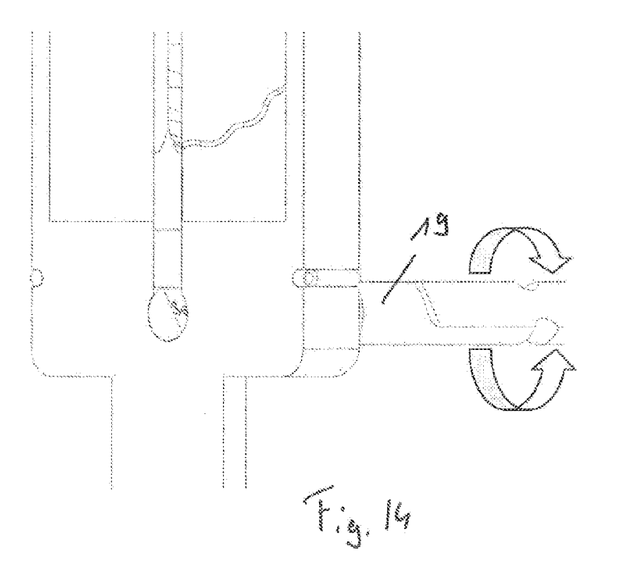
Figure 15:
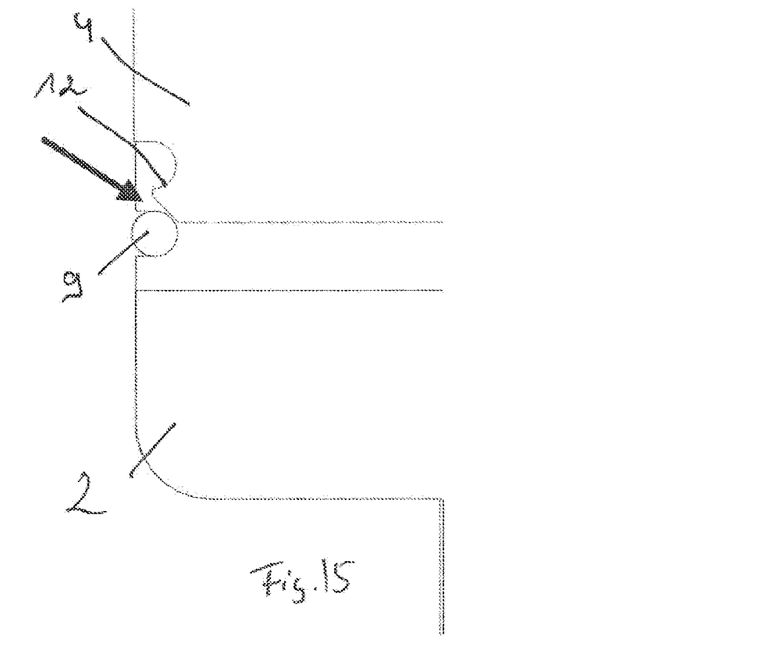
Figure 16:
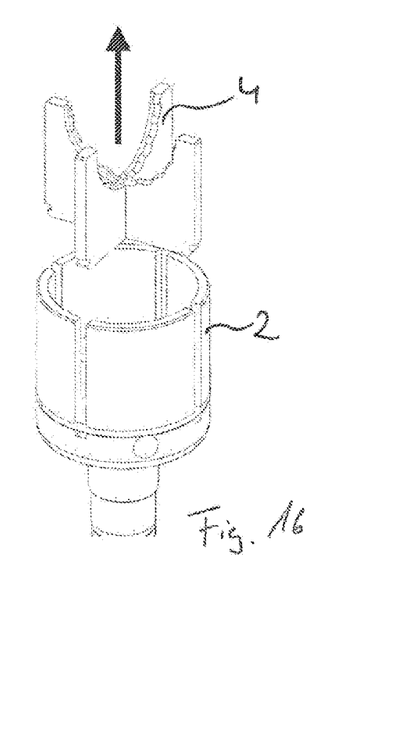

As can be seen from FIGS. 13 and 14, the releasing tool 19, by twisting about its longitudinal extent axis, comes in contact with the milling cutter 4 and acts upon the latter in axial direction upwards, whereby owing to the curvature of the detent recess 12 a radial force component results onto the spring element 9, acts upon the latter again temporarily with force in radial direction outwards during the releasing process and is tensioned and thus the milling cutter 4 comes free from the engagement, as is shown in FIG. 15. There, the spring element is in the relaxed or respectively more relaxed state again and the free milling cutter 4 can be removed axially as shown in FIG. 16.

Figure 17:
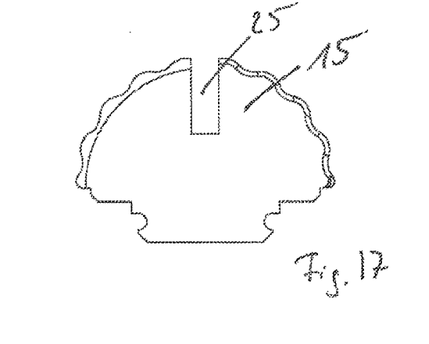
FIG. 17 to FIG. 22: different individual parts and details of embodiments of a convex milling cutter for the production of concave millings.
Figure 18:
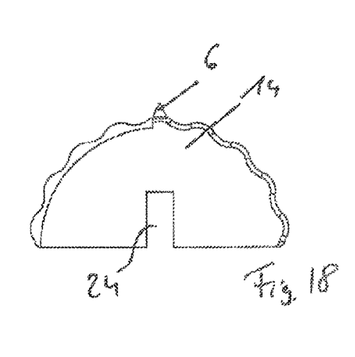
Figure 19:
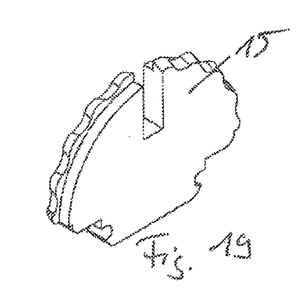
Figures 20, 21:
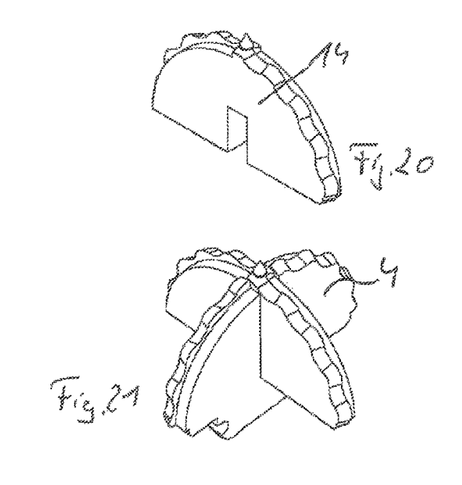

Different parts and embodiments of convex milling cutters 4 are illustrated in FIG. 17 to 22. Here, FIGS. 17 and 19 show a lower second cutter part 15, and FIGS. 18 and 20 show the upper (first) cutter part 14 matching it. The first cutter part 14 has a lower cut-out 24 in the width of the second cutter part 15. A corresponding cut-out 25, opposed to the cut-out 24, in the width of the first cutter part 14 is provided in the cutter part 15, so that the cutter parts 14, 15, as shown in FIG. 21 and their cut-outs 24, 25 are able to be inserted into one another and therefore describe a convex covering contour. As already mentioned several times, the cutter parts 14, 15 can be constructed so as to be able to be inserted into one another or onto one another detachably, for example secured by gluing or welding or produced in a single piece.

Figure 22:
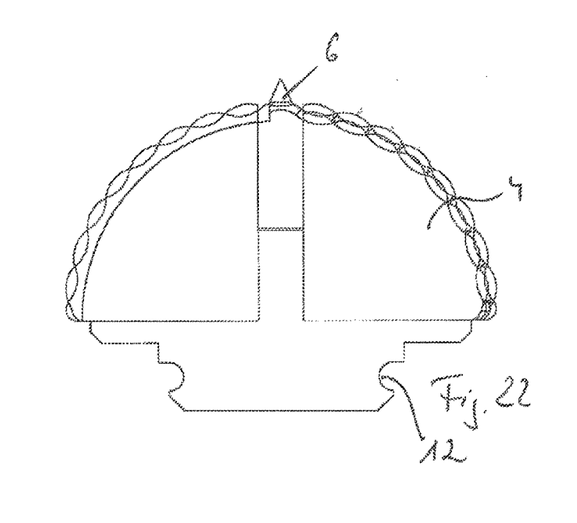

In the example embodiment which is shown, the second cutter part 15 according to FIG. 17 is constructed asymmetrically with regard to its blade sections, whereas the first cutter part according to FIG. 18 is configured symmetrically. Embodiments are also able to be realized in which both cutter parts are constructed symmetrically or both cutter parts are constructed asymmetrically. FIG. 22 shows a milling cutter 4, which is composed of an asymmetrical second and a symmetrical first cutter part.

Figures 23, 24, 28:
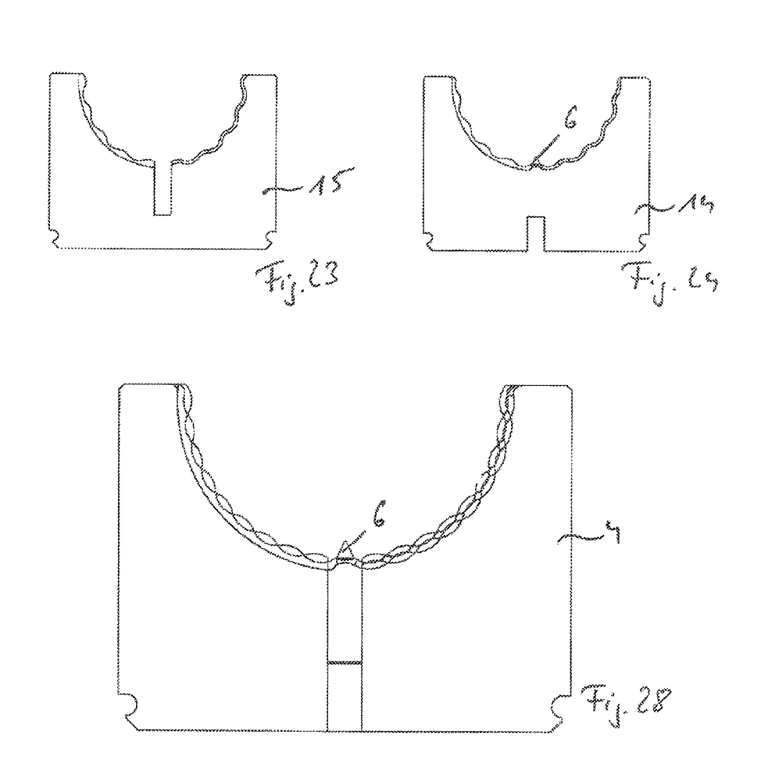
FIG. 23 to FIG. 28: different individual parts and embodiments of a concave milling cutter for the production of convex millings.
Figure 25:
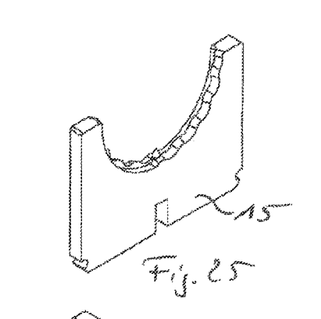
Figure 26:
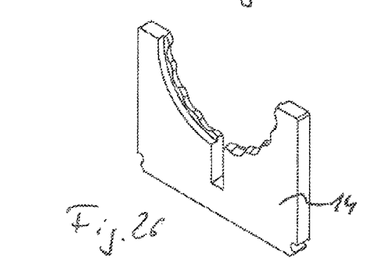
Figure 27:
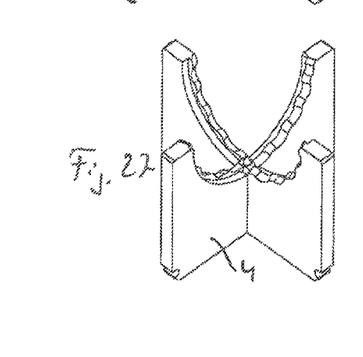

In an analogous manner, FIG. 23 to 28 show different components or respectively embodiments of a concave cutter part 4, wherein FIGS. 23 and 25 show a second cutter part and FIG. 24 shows an associated first cutter part 14, which are able to be placed together intersecting one another in the manner as the cutter part according to FIG. 17 to 22. The cutter part according to FIG. 23 is constructed asymmetrically with regard to its two blade sections, whereas the first cutter part 14 according to FIG. 24 is configured symmetrically. FIG. 28 shows a milling cutter 4 composed from these two cutter parts 14, 15. All milling cutters according to FIG. 17 to 28 have a serration.

The invention claimed is:

1. A surgical bone milling tool for the arthrodesis of a metatarsophalangeal joint comprising:

a rotatable milling cutter holder, the milling cutter holder operable to rotate relative to a bone of the metatarsophalangeal joint during a bone milling procedure; and at least one milling cutter for the production of a concave or convex milling contour in a bone;

wherein the milling cutter is removably fixed on the milling cutter holder by a fixing element that provides for detachable engagement of the milling cutter on the milling cutter holder, the fixing element comprising a spring element that extends peripherally around and engages at least a portion of an outer surface of the milling cutter holder, and wherein in an attached state the milling cutter and the milling cutter holder are rotationally fixedly coupled together, such that the milling cutter is incapable of rotating relative to the milling cutter holder, to allow simultaneous rotation of the milling cutter with the milling cutter holder.

2. The bone milling tool according to claim 1, wherein the spring element is constructed and arranged such that the spring element is able to be tensioned in a radial direction on engaging and/or releasing of the milling cutter, and in the engaged state is received into a spring element recess.

3. The bone milling tool according to claim 1, wherein the spring element is secured in a groove of the milling cutter holder and on engaging of the milling cutter is tensioned by direct interaction with the milling cutter.

4. The bone milling tool according to claim 3, wherein the milling cutter penetrates the spring element in the engaged state axially inwards or embraces it externally.

5. The bone milling tool according to claim 1, wherein the spring element comprises a slotted spring ring.

6. The bone milling tool according to claim 1, wherein the spring element comprises part-ring-shaped springs, spaced apart in peripheral direction.

7. The bone milling tool according to claim 1, wherein a leading chamfer is provided for radial tensioning on the milling cutter.

8. The bone milling tool according to claim 1, wherein a tool mount for a mount of a releasing tool is provided on the milling cutter holder, wherein the milling cutter extends into the mount perpendicularly to a longitudinal extent of the mount, such that the milling cutter, by twisting of the releasing tool in the mount, is able to be acted upon by force axially in a releasing direction.

9. The bone milling tool according to claim 1, further comprising a form-fitting means for securing the milling cutter against rotation relative to the milling cutter holder.

10. The bone milling tool according to claim 9, wherein the form-fitting means comprises at least one axial guide for guiding the milling cutter for securing and/or releasing the milling cutter.

11. The bone milling tool according to claim 10, wherein the spring element penetrates the form-fitting means in peripheral direction.

12. The bone milling tool according to claim 11, wherein the milling cutter is constructed with at least two cutter parts which are able to be inserted into one another axially.

13. The bone milling tool according to claim 1, wherein the milling cutter has a serration.

14. The bone milling tool according to claim 1, wherein the milling cutter has cutter parts intersecting one another at right angles.

15. The bone milling tool according to claim 1, wherein the milling cutter has a centering point.

16. An assorted set comprising a bone milling tool according to claim 1 with a first milling cutter and at least a second milling cutter, differing from the first milling cutter, by having a different diameter.

17. The bone milling tool according to claim 1, wherein the spring element is receivable within at least one spring element recess formed in the milling cutter.

18. A surgical bone milling tool for the arthrodesis of a metatarsophalangeal joint comprising:

a rotatable milling cutter holder, the milling cutter holder operable to rotate relative to a bone of the metatarsophalangeal joint during a bone milling procedure; and at least one milling cutter for the production of a concave or convex milling contour in a bone;

wherein the milling cutter is removably fixed on the milling cutter holder by a fixing element that provides for detachable engagement of the milling cutter on the milling cutter holder, the fixing element comprising a spring element, and wherein in an attached state the milling cutter and the milling cutter holder are rotationally fixedly coupled together to allow simultaneous rotation of the milling cutter with the milling cutter holder; and wherein the spring element extends peripherally around and engages at least a portion of an outer surface of the milling cutter holder.

19. A surgical bone milling tool for the arthrodesis of a metatarsophalangeal joint comprising:

a rotatable milling cutter holder, the milling cutter holder operable to rotate relative to a bone of the metatarsophalangeal joint during a bone milling procedure; and at least one milling cutter for the production of a concave or convex milling contour in a bone;

wherein the milling cutter is removably fixed on the milling cutter holder by a fixing element that provides for detachable engagement of the milling cutter on the milling cutter holder, the fixing element comprising a spring element that extends peripherally around and engages at least a portion of an outer surface of the milling cutter holder, and wherein in an attached state the milling cutter and the milling cutter holder are rotationally fixedly coupled together, such that the milling cutter is secured against rotation relative to the milling cutter holder, to allow simultaneous rotation of the milling cutter with the milling cutter holder.

* * * * *

UNITED STATES PATENT AND TRADEMARK OFFICE
CERTIFICATE OF CORRECTION

PATENT NO. : 9,517,078 B2
APPLICATION NO. : 13/747982
DATED : December 13, 2016
INVENTOR(S) : Uwe Pech Page 1 of 1

It is certified that error appears in the above-identified patent and that said Letters Patent is hereby corrected as shown below:

On the Title Page

In item (73), in "Assignee", in Column 1, Line 1, delete "GMBH" and insert --GMBH, Winterthur--, therefor In item (30), in "Foreign Application Priority Data", in Column 1, Line 1, delete "10 2012 100 565" and insert --10 2012 100 565.6--, therefor In the Claims In Column 10, Line 7, in Claim 15, delete "centering" and insert --centring--, therefor Signed and Sealed this
Thirteenth Day of November, 2018

Andrei Iancu
*Director of the United States Patent and Trademark Office*